US006297194B1

(12) United States Patent
Miller et al.

(10) Patent No.: US 6,297,194 B1
(45) Date of Patent: Oct. 2, 2001

(54) PRODUCTION OF PHOSPHONOPYRAZOLES

(75) Inventors: Paula C. Miller; Jane M. Curtis; John M. Molyneaux, all of St. Louis; Thomas J. Owen, Chesterfield, all of MO (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 09/497,017

(22) Filed: Feb. 2, 2000

Related U.S. Application Data

(60) Provisional application No. 60/118,408, filed on Feb. 2, 1999.

(51) Int. Cl.[7] .................................................. A01N 57/24
(52) U.S. Cl. .......................................... 504/197; 47/58.1
(58) Field of Search ............................................... 504/197

(56) References Cited

U.S. PATENT DOCUMENTS

| | | |
|---|---|---|
| 3,576,814 | 4/1971 | Seidel et al. . |
| 4,028,084 | 6/1977 | McNulty et al. . |
| 4,038,065 | 7/1977 | Johnson et al. . |
| 4,051,142 | 9/1977 | Carlson . |
| 4,115,101 | 9/1978 | Carlson . |
| 4,238,220 | 12/1980 | Carlson . |
| 4,345,934 | 8/1982 | Fujimoto . |
| 4,604,134 | 8/1986 | Labovitz et al. . |
| 4,623,378 | 11/1986 | Dürrr et al. . |
| 4,707,181 | 11/1987 | Patterson . |
| 4,714,491 | 12/1987 | Prisbylla . |
| 4,729,782 | 3/1988 | Labovitz et al. . |
| 4,732,603 | 3/1988 | Patterson . |
| 4,735,649 | 4/1988 | Dhingra et al. . |
| 4,747,871 | 5/1988 | Ruminski et al. . |
| 4,925,477 | 5/1990 | McDaniel . |
| 4,936,904 | 6/1990 | Carlson . |
| 4,962,199 | 10/1990 | Yalamanchili . |
| 4,966,623 | 10/1990 | Ackmann et al. . |
| 5,010,192 | 4/1991 | Yelland et al. . |
| 5,062,880 | 11/1991 | Patterson . |
| 5,129,939 | 7/1992 | Labovitz et al. . |
| 5,169,429 | 12/1992 | Warner et al. . |

FOREIGN PATENT DOCUMENTS

| | | |
|---|---|---|
| 930 212 | 7/1955 | (DE) . |
| 28 08 795 | 9/1978 | (DE) . |
| 34 02 308 | 8/1985 | (DE) . |
| 4139849 | 6/1992 | (DE) . |
| 037 133 | 10/1981 | (EP) . |
| 049 971 | 4/1982 | (EP) . |
| 055 061 | 6/1982 | (EP) . |
| 138 662 | 4/1985 | (EP) . |
| 244 075 | 11/1987 | (EP) . |
| 276 204 | 7/1988 | (EP) . |
| 363 236 | 12/1994 | (EP) . |
| 1 603 896 | 12/1981 | (GB) . |
| 6-99252 | 12/1994 | (JP) . |

OTHER PUBLICATIONS

Aboujaoude et al., Dialkyl FormylMethylphosphonates α–Fonctionnels–II[1], *Tetrahedron* 41(2):427–433 (1985).

Katagiri et al., 3–Acetoxy–2–dimethylphosphonoacrylates. New Dienophiles and Their Use for the Synthesis of Carbocyclic C–Nucleoside Precursors by the Aid of RRA Reaction, *Chemistry Letters* 1855–1858 (1990).

Khotinen et al., An Efficient Synthesis of 4–Dimethoxyphosphonyl Substituted Pyrazoles and Pyrazoline–5–Ones, *Phosphorus, Sulfur, and Silicon* 83:53–58 (1993).

Lynch et al., Synthesis and Gametocidal Activity of 1–Aryl–5–(aminocarbonyl)–1H–pyrazole–4–carboxylic Acids, *American Chemical Society* 504:200–211 (1992).

Neidlein et al., [(1,3–Dioxolan–2–yliden)methyl] phosphonate und—phosphinate als (einfache) Synthone in der Heterocyclensynthese, *Helvetica Chimica Acta* 75:124–136 (1992).

Nifant'ev et al., Synthesis of phosphorylated pyrazolones, *Khim. Geterotsikl. Soedin* 4:513–516 (1977) (Russian) (SciFinder Abstract in English Included).

Polozov et al., Insertion of Carbenes into P–H Bonds. 5. Synthesis of New Phosphonates and Phosphinates in Reactions Catalysed by Cu, Pd, Rh, Ni Complexes, *Phosphorus, Sulfur, and Silicon* 73:153–159 (1992).

Tschabold et al., Crop Breeding, Genetics, & Cytology, *Crop Science* 28(4):583–588 (1988).

Miller et al., "One–Pot" Synthesis of Dimethyl [1–Substituted–5–Hydroxy–1H–Pyrazol–4–YL]Phosphonates, *Organic Preparation and Procedures Int* 31:295–304 (1999).

Nifant'ev et al., Synthesis of phosphorylated pyrazolones, *Journal of Heterocyclic Chemistry* 4:414–416 (1977) (English Translation).

*Primary Examiner*—Robert W. Ramsuer

(57) ABSTRACT

Pyrazole compounds with activity as chemical hybridizing agents and methods for synthesis of such compounds are disclosed. These compounds are useful in producing hybrid wheat (*Triticum aesativum*) and other crops.

4 Claims, No Drawings

PRODUCTION OF PHOSPHONOPYRAZOLES

This application claims priority to U.S. Provisional Application No. 60/118,408, filed Feb. 2, 1999, incorporated herein in its entirety.

FIELD OF THE INVENTION

The invention relates to a method for the production of phosphonopyrazole compounds and related compositions and methods.

BACKGROUND OF THE INVENTION

Cross-fertilization of closely related plants can result in progeny that have a desirable combination of traits not possessed by either inbred parent. This phenomenon, known as heterosis or hybrid vigor has been identified in major crop species (Stuber, *Plant Breeding Rev.* 12:29–65, 1994). Hybrid plants often have substantially superior agronomic performance characteristics, including, for example, plant size, grain yield, disease resistance, herbicide tolerance, and climatic adaptation.

A major limitation in the production of hybrid seed for most crop species is the lack of simple, reliable and economical methods of generating male-sterility while leaving female gametes intact and accessible for cross-pollination by a suitable pollen donor. Gametocides, or chemical hybridizing agents (CHAs), are useful not only for producing hybrid plants but also for controlling gene flow from a genetically modified crop plant to related wild species.

In some plants, such as corn, physical removal of the organ containing male gametes is relatively straightforward because the organ is both exposed and spatially separated from the female gametes. However, most crop species have both functional male and female organs within the same flower, so that emasculation is neither simple nor straightforward, making this process labor intensive and expensive. Furthermore, it is difficult to ensure the complete absence of self-pollination through these approaches.

Several naturally occurring genetic mechanisms of male sterility have been exploited for the production of hybrid seed in some plant species, including various cytoplasmic male sterility (CMS) systems. A disadvantage of strategies involving CMS is that they require three distinct lines to produce a single crossed hybrid: the male-sterile female parent line; a maintainer line that is isogenic to the male-sterile line but contains fully functional mitochondria; and the male parent line. Many CMS types have unfavorable characteristics that eliminate or restrict their use, including undesirable linked or pleiotropic characteristics such as disease susceptibility, breakdown of sterility, and inconsistent and/or complexly inherited fertility restoration. Furthermore, CMS systems are unavailable in many important crop species.

Chemical gametocides have been described, including pyridines (EP 0 276 204), pyridones and pyridazines (U.S. Pat. Nos. 4,115,101 and 4,345,934), glyphosate (U.S. Pat. No. 4,735,649), 5-oxy- or amino-substituted cinnoline (U.S. Pat. No. 5,129,939), pyridazine (U.S. Pat. Nos. 5,062,880 and 4,345,934), diazabicyloctane (U.S. Pat. No. 4,925,477) and N-alkyl-4-oxonicotinate compounds (U.S. Pat. No. 4,714,492). One commercial male gametocide for wheat, Genesis® (Monsanto Company, St. Louis, Mo.; see U.S. Pat. No. 5,062,880), is an effective gametocide and is the standard for comparison and development of new gametocides for wheat. In addition, some phosphonyl-substituted pyrazoles, including some 3-hydroxy(alkoxy)-pyrazole-4-ylphosphonates, have systemic movement in plants and have been reported to be useful as insecticides in plants; however, this class of compounds was said to be nonphytotoxic and no gametocidal activity was reported (DE 4139849).

Few chemical hybridizing agents (CHAs) have been used for the commercial production of hybrid seed, primarily because of their lack of selectivity for gametes in general, and for male gametes in particular. Systemic movement and selective phytotoxic activity are necessary requirements for an effective gametocide. Many compounds destroy or impair male gametes of a plant but also kill female gametes and vegetative tissues. Compounds that selectively target the gametes to a greater extent than vegetative tissues are generally non-discriminating regarding the sex of the gametes destroyed. In addition, many chemical gametocides with good selectivity have toxicological issues or other environmental issues that limit the use of these compounds for production of commercial levels of hybrid seeds.

Genetic engineering has also resulted in strategies for causing male sterility, such as the use of protoxin (U.S. Pat. No. 5,254,801) and antisense (U.S. Pat. No. 5,728,926) technology.

Other desirable characteristics may be dictated by the plant to be treated. For example, in the case of wheat, male and female gametes are found inside the same flower, which remains closed until the male gametes release their pollen onto the female gametes. When the flower opens, self-fertilization is normally essentially complete. A useful wheat gametocide must kill the male gametes but not interfere with floral opening when the female gametes are ready to be fertilized, so that fertilization by pollen from other wheat plants can occur. The need for effective wheat gametocides or chemical hybridizing agents for wheat has been the subject of extensive research (Tschabold et al., *Crop Science* 28:583–588, 1988).

SUMMARY OF THE INVENTION

We have developed a novel process for production of phosphonopyrazole compounds by contacting an alkaline salt of 3-hydroxy-2-(dialkyl phosphono)acrylate and either a protonated hydrazine, a protonated alkyl hydrazine, or a protonated aryl hydrazine. In a preferred embodiment, the method involves addition of a base followed by acidification. This method has several advantages as compared with published cyclocondensation reactions. It is simpler as there is no purification step it and can be performed with an aqueous solvent (although organic solvents or combinations of aqueous and organic solvents can be employed). In addition, the intermediates are stable at room temperature indefinitely. Moreover, this method is more efficient and higher yielding. Examples of phosphonopyrazoles that can be used in such processes are dialkyl [1-aryl or alkyl-(3 or 5)-hydroxy-1H-pyrazole-4-yl]phosphonates, which can be used as reactants to produce dialkyl [1-aryl or aryl-(3 or 5)-hydroxy-1H-pyrazol-4-yl]phosphonates having gametocidal activity, for example.

According to one process of the invention, the alkaline salt of 3-hydroxy-2-(dialkyl phosphono)acrylate and the selected hydrazine are reacted in an aqueous medium. For ease of purification of the product of the process, the aqueous phase is washed with an organic solvent to remove impurities before acidification.

According to another aspect of the invention, the phosphonopyrazole employed in such a process is a compound of formula I or II:

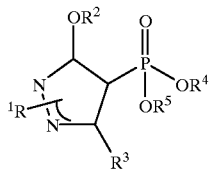

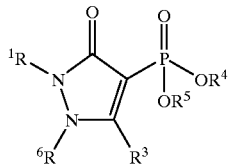

wherein: $R^1$ is alkyl, aryl, heteroaryl, benzyl or C3–C8 cycloalkyl, preferably C3–C7 cycloalkyl; $R^2$ is hydrogen or an alkaline salt; $R^3$ is hydrogen, alkyl, aryl or heteroaryl; $R^4$ is hydrogen, alkyl, phenyl, or a salt; $R^5$ is hydrogen, alkyl, phenyl, or a salt; $R^6$ is alkyl, aryl or heteroaryl; alkyl is C1–C8, preferably C1–C4 branched or C1–C4 straight chains; aryl is phenyl or naphthyl optionally substituted with 1–5 groups, preferably 1–3 groups, selected from halogen, trihalomethyl, C1–C8 alkyl (straight or branched chain), C1–C8 alkoxy (straight or branched chain), nitro and cyano; benzyl is benzyl optionally substituted with 1–3 groups selected from halogen, trihalomethyl, C1–C8 alkyl (straight or branched chain), C1–C8, preferably C4 alkoxy (straight or branched chain), nitro and cyano; and heteroaryl is pyridyl optionally substituted with 1–4 groups selected from halogen, trihalomethyl, C1–C8 alkyl (straight or branched chain), C1–C8 alkoxy (straight or branched chain), nitro and cyano.

According to another aspect of the invention, compounds of formula I or II (as shown above) are provided wherein: $R^1$ is hydrogen, alkyl, aryl, heteroaryl, benzyl or C3–C8 cycloalkyl, preferably C3–C7 cycloalkyl; $R^2$ is hydrogen, alkyl, benzyl, C1–C8 alkenyl, preferably C1–C4 alkenyl, or a salt (preferably an agronomically acceptable salt such as an alkali metal salt or an amine salt, for example); $R^3$ is hydrogen, alkyl, aryl or heteroaryl; $R^4$ is hydrogen, alkyl, phenyl, or a salt; $R^5$ is hydrogen, alkyl, phenyl, or a salt; $R^6$ is alkyl, aryl or heteroaryl; alkyl is C1–C8, preferably C1–C4 branched or C1–C4 straight chains; aryl is phenyl or naphthyl optionally substituted with 1–5 groups, preferably 1–3 groups, selected from halogen, trihalomethyl, C1–C8 alkyl (straight or branched chain), C1–C8 alkoxy (straight or branched chain), nitro and cyano; benzyl is benzyl optionally substituted with 1–3 groups selected from halogen, trihalomethyl, C1–C8 alkyl (straight or branched chain), C1–C8, preferably C4 alkoxy (straight or branched chain), nitro and cyano; and heteroaryl is pyridyl optionally substituted with 1–4 groups selected from halogen, trihalomethyl, C1–C8 alkyl (straight or branched chain), C1–C8 alkoxy (straight or branched chain), nitro and cyano; provided that when $R^3$ is hydrogen and $R^1$ is aryl, $R^2$ is not hydrogen or C1–C4 alkyl.

Examples of compounds of the present invention are the following: dimethyl [1-cyclohexyl-5-hydroxy-1H-pyrazol-4-yl]phosphonate, dimethyl [1-(4-chlorophenyl)-5-hydroxy-3-phenyl-1H-pyrazol-4-yl]phosphonate, dimethyl [1-(3,5-dimethylphenyl)-5-hydroxy-3-phenyl-1H-pyrazol-4-yl]phosphonate, dimethyl{1-(4-chlorophenyl)-5-[(4-chlorobenzyl)oxy]-1H-pyrazol-4-yl} phosphonate, dimethyl{1-(4-chlorophenyl)-5-[(2-nitrobenzyl)oxy]-1H-pyrazol-4-yl} phosphonate, 2-(4-chlorophenyl)-3-[2-nitrobenzyl)oxy]-1H-pyrazol-4-yl]phosphonic acid, dimethyl [2-(4-chlorophenyl)-2,3-dihydro-1-ethyl-3-oxo-pyrazol-4-yl]phosphonate, dimethyl [2-(4-chlorophenyl)-1-cyclohexyl-2,3-dihydro-3-oxo-pyrazol-4-yl]phosphonate, dimethyl [2-(3,5-dimethylphenyl)-2,3-dihydro-1-ethyl-3-oxo-pyrazol-4-yl]phosphonate, and dimethyl [1-butyl-2-(3,5-dimethylphenyl)-2,3-dihydro-3-oxo-pyrazol-4-yl] phosphonate.

According to another aspect of the invention, compositions are provided for inducing male sterility in plants, such compositions comprising a gametocidally effective amount of a compound of formula I or II (as shown above) and an agronomically acceptable carrier, wherein: $R^1$ is hydrogen, alkyl, aryl, heteroaryl, benzyl or C3–C8 cycloalkyl, preferably C3–C7 cycloalkyl; $R^2$ is hydrogen, alkyl, benzyl, or C1–C8 alkenyl, preferably C1–C4 alkenyl, or an agronomically acceptable salt; $R^3$ is hydrogen, alkyl, aryl or heteroaryl; $R^4$ is hydrogen, alkyl, phenyl, or an agronomically acceptable salt; $R^5$ is hydrogen, alkyl, phenyl, or an agronomically acceptable salt; $R^6$ is alkyl, aryl or heteroaryl; alkyl is C1–C8, preferably C1–C4 branched or C1–C4 straight chains; aryl is phenyl or naphthyl optionally substituted with 1–5 groups, preferably 1–3 groups, selected from halogen, trihalomethyl, C1–C8 alkyl (straight or branched chain), C1–C8 alkoxy (straight or branched chain), nitro and cyano; benzyl is benzyl optionally substituted with 1–3 groups selected from halogen, trihalomethyl, C1–C8 alkyl (straight or branched chain), C1–C8, preferably C4 alkoxy (straight or branched chain), nitro and cyano; and heteroaryl is pyridyl optionally substituted with 1–4 groups selected from halogen, trihalomethyl, C1–C8 alkyl (straight or branched chain), C1–C8 alkoxy (straight or branched chain), nitro, and cyano. According to one embodiment of such compositions, if $R^3$ is hydrogen and $R^1$ is aryl, then $R^2$ is not hydrogen or C1–C4 alkyl.

Among the gametocidal compositions of the invention are compositions that include one or more of the following compounds: dimethyl [1-(4-chlorophenyl)-5-hydroxy-1H-pyrazol-4-yl]phosphonate, dimethyl [1-(4-fluorophenyl)-5-hydroxy-1H-pyrazol-4-yl]phosphonate, dimethyl [1-(2-chlorophenyl)-5-hydroxy-1H-pyrazol-4-yl]phosphonate, dimethyl [1-(4-bromophenyl)-5-hydroxy-1H-pyrazol-4-yl] phosphonate, dimethyl [1-cyclohexyl-5-hydroxy-1H-pyrazol-4-yl]phosphonate, dimethyl [1-(4-chlorophenyl)-5-hydroxy-3-phenyl-1H-pyrazol-4-yl]phosphonate, dimethyl [1-(3,5-dimethylphenyl)-5-hydroxy-3-phenyl-1H-pyrazol-4-yl]phosphonate, dimethyl{1-(4-chlorophenyl)-5-[(4-chlorobenzyl)oxy]-1H-pyrazol-4-yl}phosphonate, dimethyl{1-(4-chlorophenyl)-5-[(2-nitrobenzyl)oxy]-1H-pyrazol-4-yl}phosphonate, methyl [2-(3,5-dimethylphenyl)-3-hydroxy-1H-pyrazol-4-yl]phosphonate, methyl [2-(4-chlorophenyl)-3-hydroxy-1H-pyrazol-4-yl]phosphonate, 2-(4-chlorophenyl)-3-[2-nitrobenzyl)oxy]-1H-pyrazol-4-yl]phosphonic acid, 2-(4-chlorophenyl)-3-hydroxy-1H-pyrazol-4-ylphosphonic acid, 2-(3,5-dimethylphenyl)-3-hydroxy-1H-pyrazol-4-ylphosphonic acid, dimethyl [1-(4-bromophenyl)-3-hydroxy-1H-pyrazol-4-yl]phosphonate, dimethyl [2-(4-chlorophenyl)-2,3-dihydro-1-ethyl-3-oxo-pyrazol-4-yl]phosphonate, dimethyl [2-(4-chlorophenyl)-1-cyclohexyl-2,3-dihydro-3-oxo-pyrazol-4-yl]phosphonate, dimethyl [2-(3,5-dimethylphenyl)-2,3-dihydro-1-ethyl-3-oxo-pyrazol-4-yl]phosphonate, dimethyl [1-butyl-2-(3,5-dimethylphenyl)-2,3-dihydro-3-oxo-pyrazol-4-yl] phosphonate, methyl potassium[2-(3,5-dimethylphenyl)-3-hydroxy-1H-pyrazol-4-yl]phosphonate, methyl potassium [4-chlorophenyl-3-hydroxy-1H-pyrazol-4-yl]phosphonate, and hydrogen potassium[2-(3,5-dimethylphenyl)-3-hydroxy-1H-pyrazol-4-yl]phosphonate. The present invention also encompasses plants that has been rendered substantially male-sterile by treatment with such gametocidal compositions and seed treated with such gametocidal compositions.

According to another aspect of the invention, methods are described for inducing male sterility in a plant, such as a monocot (including graminaceous monocots such as wheat) that include treating the plant or a seed thereof with such a gametocidal composition.

According to another aspect of the invention, methods are described for producing hybrid seed that include the steps of treating a female parent of a plant prior to meiosis with a gametocidal composition of the invention, pollinating the female parent with pollen from an untreated male parent that is of a different line from the female parent, and allowing the female parent to produce the hybrid seed. According to one embodiment, the female parent plant is treated by applying from about 1/32 pound to about 10 pounds of the gametocidal composition per acre (about 0.035 to about 11.2 Kg/ha), for example to foliage of the female parent plants. Alternatively, hybrid seed are produced by treating seed with a gametocidal composition of the invention, growing the seed to produce a substantially male-sterile female parent plant; pollinating the female parent with pollen from an untreated male parent that is of a different line from the female parent, and allowing the female parent to produce the hybrid seed. The present invention also encompasses hybrid seed produced by such methods.

DETAILED DESCRIPTION OF THE INVENTION

We describe herein improved methods for producing 2,3-dihydro-3-oxo-pyrazol-4-yl phosphonates and hydroxy or alkoxy-1H-pyrazol-4-yl phosphonates and novel compounds produced by such methods that are useful, for example, as gametocides. The methods taught herein are simpler than comparable published cyclocondensation reactions (Khotinen and Polozov, *Phosphorous, Sulfur Silicon Relat. Elem.* 83:53, 1990; Nifant'ev et al., *Khim. Geterotsikl. Soedin.* 513, 1977; Polozov et al., *Phosphorous, Sulfur, Silicon Relat. Elem.*, 73:153, 1992; Aboujaoude et al. 1985. *Tetrahedron* 41:427, 1985), because no purification step is required and the reactions can be performed with an aqueous solvent. In addition, the intermediates are stable at room temperature indefinitely. Moreover, this method is more efficient and higher yielding.

Compounds of the invention are useful, for example, in preventing the production of viable pollen in plants and thus in preventing the distribution of pollen from a plant treated with the compound to other plants, including related crop species and wild species.

Pollen from crop plants in which the vegetative parts of the plant are the primary agricultural product (e.g., alfalfa, canola, carrot, cotton, sunflower, soybean, sugar beet, tomato, cucumber, melon) and various ornamental plants can be reduced or eliminated by application of the gametocidal compositions of the invention. When applied to self-pollinated wild plants, such gametocidal compositions reduce or eliminate seed production. This aspect of the invention in combination with herbicide formulations can functionally increase the effectiveness of herbicides by reducing the amount of seeds produced from the treated plants. The resulting herbicide formulation has a broader spectrum of activity.

As used herein, the term "male sterility" includes sterility caused by lack of male flower parts, by formation of sterile pollen, and by male flower parts that produce pollen that has a normal appearance but that is functionally unable to cause pollination.

A "gametocide" is a compound that, when applied to a plant, is capable of killing or altering or terminating the development of the plant's male gametes, thereby rendering the plant substantially male sterile, while leaving at least a significant proportion of the plant's female gametes capable of being cross-fertilized with a subsequent high yield of fertile, viable seed. For an ideal gametocide, the application level effectively destroys male gametes but is significantly lower than the level that is required to destroy female gametes. Gametocidal compositions are thereful useful as chemical hybridizing agents for use in plant breeding programs. Such a gametocide can be applied in the field by spraying without the need for extraordinary precautions to prevent substantial reductions in female fertility.

"Outcrossing" is the exchange of genetic information from one plant to another by the spread of pollen.

Compounds according to the invention are useful as gametocides or CHAs for use in production of hybrid dicotyledonous crops (including, but not limited to, sugar beet, sugarcane, potato, sweet potato, lettuce cabbage, tea, radish, turnips, garlic and onion) and monocotyledonous crops, including, but not limited to, graminaceous crops such as wheat, barley, maize, rice, sorghum, millet, oats, rye, triticale, turf and forage grasses, etc. Compounds of the present invention induce selected male sterility without also inducing unacceptable female sterility. About 30% female fertility is generally acceptable, although this level may differ when the method is used commercially, based on the economics of $F_1$ seed production. For use as CHAs, compounds according to the invention are generally applied at a rate of from about 1/32 to about 20 pounds per acre (0.035 to 22.4 Kg/ha), preferably from about 1/8 to about 10 pounds per acre (0.14 to 11.2 Kg/ha). The amount used depends upon the crop being treated, the compound being used, and the method of application and can be determined empirically.

Any conventional method of hybridization may be used. For example, the two parent strains to be crossed are planted in alternate sections, rows, or groups of rows. The female parent is treated with a compound according to the invention in order to render the female parent male sterile. Pollen from the male (untreated) parent then fertilizes the female parent, either by means of human intervention or by a natural process, such as wind-borne pollination. The seed produced by the female parent is an $F_1$ hybrid, which is then collected by conventional means.

One method of applying gametocidal compositions according to the invention (preferably aqueous compositions) to apply such compositions to foliage, to the soil, or to the water surface (e.g., in a rice field). Gametocidal compositions according to the invention are applied preferably between the onset of flowering and the beginning of meiosis. Such compositions can also be applied as a seed treatment, for example, by soaking seeds in a liquid formulation containing the compound according to the invention or by coating seeds with the compound. In seed treatment applications, the compounds of the invention are generally applied at a rate of about 1/4 to about 10 pounds (0.1–5 Kg) per hundred weight of seed.

According to another aspect of the invention, compositions are provided that include one or more compounds according to the invention and, optionally, other active and inactive ingredients, including other CHAs. For example, the compounds of the invention can be used in combination with plant growth regulators, such as auxins, gibberellins, ethylene-releasing agents such as ethephon, pyridones, cytokinins, maleic hydrazide, succinic acid 2,2-dimethylhydrazide, choline and its salts, (2-chloromethyl) trimethylammonium chloride, triodobenzoic acid, tributyl-2,4-dichlorobenzylphosphonium chloride, polymeric N-vinyl-2-oxazolidinones, tri(dimethylaminoethyl) phosphate and its salts, and N-dimethylamino-1,2,3,6-tetrahydrophthalamic acid and its salts, and other well-known CHAs, and under some conditions may be used advantageously with other agricultural chemicals such as herbicides, fungicides, insecticides, and plant bactericides.

A compound of the invention can be applied to the growth medium or to plants to be treated either by itself or as a component of a formulation that also includes an agronomically acceptable carrier and optionally other active ingredients, including other compounds of the invention. By "agronomically acceptable carrier" is meant any liquid or solid substance that can be used to dissolve, disperse, or diffuse a compound in the composition without impairing the effectiveness of the compound and which by itself has no significant detrimental effect on the soil, equipment, crops, or agronomic environment. Such compositions include liquid or solid formulations or solutions, including wettable powders, emulsifiable concentrates, dusts, granules, pellets, aerosols, flowable emulsion concentrates, suspensions, and solutions, which may be prepared according to any conventional method. A composition containing a compound of the invention can be diluted with an agronomically suitable liquid or solid carrier. Such compositions can also include one or more agronomically acceptable adjuvants such as anionic, cationic, or nonionic surface-active agents (wetting agents, spreading agents, dispersing agents, suspending agents, and emulsifying agents), conditioning agents, sticking agents, adhesives, etc. Examples of useful adjuvants can be found in "Detergents and Emulsifier's Annual" (John W. McCutcheon, Inc.).

Preferred compositions include liquids and wettable powders, preferably containing as a conditioning agent one or more surface-active agents in amounts sufficient to render the active ingredient(s) readily dispersible in water or in oil. The incorporation of a surface-active agent into the compound can enhance its efficacy. Suitable wetting agents include but are not limited to alkyl benzene and alkyl naphthalene sulfonates, sulfonated fatty alcohols, amines or acid amides, long chain acid esters of sodium isothionate, esters of sodium sulfonsuccinate, sulfated or sulfonated fatty acid esters, petroleum sulfonates, sulfonated vegetable oils, ditertiary acetylenic glycols, polyoxyethylene derivatives or alkylphenyls (particularly isooctylphenol and nonylphenol) and polyoxyethylene derivatives of the nono-higher fatty acid esters of hexitol anhydrides (e.g., sorbitan). Surfactants include, but are not limited to, the dihexyl ester of sodium sulfonsuccinic acid, POE 20 sorbitan monolaurate, and octylphenoxy polyethoxy ethanol. Wettable powders or dispersable granules are water-dispersible compositions containing one or more active ingredients, an inert solid extender, and one or more wetting and dispersing agents. The inert solid extenders are usually of mineral origin such as the natural clays, diatomaceous earth, salts and synthetic minerals, derived from silica and the like. Examples of such extenders include kaolinites, attapulgite clay, salts and synthetic magnesium silicate.

Compounds of the invention can be dissolved in any suitable solvent, including but not limited to one or a mixture of the following: water, alcohols, ketones, aromatic hydrocarbons, halogenated hydrocarbons, dimethylformamide, dioxane, and dimethylsulfoxide. The concentration of the active ingredient in the resulting solution is preferably from about 2% to about 98% by weight and more preferably from about 20% to about 75% by weight.

In order to produce emulsifiable concentrates, the compounds of the invention are dissolved in an organic solvent such as benzene, toluene, xylene, methylated naphthalene, corn oil, turpentine, o-dichlorobenzene, isophorone, cyclohexane, or methyl oleate, or mixtures thereof, together with a conventional emulsifying agent that allows dispersion in water, e.g., ethylene oxide derivatives of alkylphenols or long-chain alcohols, mercaptans, carboxylic acids, reactive amines, and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are similarly formulated and include, in addition to the foregoing components of emulsifiable concentrates, water and a stabilizing agent such as a water-soluble cellulose derivative or a water-soluble salt of a polyacrylic acid. The concentration of the active ingredient in such emulsifiable concentrates is generally about 10% to about 60% by weight and in free-flowing emulsion concentrates is generally about 10% to about 75% by weight.

Wettable powders suitable for spraying are mixtures of a compound according to the invention, a finely divided solid (such as a clay, an organic silicate or carbonate, or a silica gel), and a wetting agent, sticking agent, and/or dispersing agent. The concentration of the active ingredient(s) in such powders is generally between about 20% and about 98% by weight and is preferably between about 40% and about 75% by weight. A dispersion agent is optionally present in an concentration of about 0.5% to about 3% by weight of the composition. A wetting agent may constitute from about 0.1% to about 5% by weight of the composition.

Dusts are mixtures of one or more compounds of the invention with finely divided inert organic or inorganic solids such as botanical flours, farina, diatomite, silicas, silicates, carbonates, and clays. One method for preparing a dust is to dilute a wettable powder with a finely divided carrier. A dust concentrate containing from about 20% to about 80% of the active ingredient(s) can be diluted to a final concentration of about 1% to about 10% by weight of the dust.

Particulate (e.g., granular) formulations are prepared by impregnating the active ingredient(s) into a solid material, such as granular fuller's earth, vermiculite, ground corn cobs, cornmeal, seed hulls (including bran or other grain hulls), or other materials. A solution of one or more of the compounds of the invention in a volatile organic solvent is sprayed or mixed with the granular solid and the solvent is removed by evaporation. The granular material can have any suitable size, preferably from about 16 to about 60 mesh. The active ingredient generally represents about 2% to about 15% by weight of the formulation. Alternatively, the formulation can be incorporated into controlled-release particulate formulations by standard methods, e.g., by encapsulation by interfacial polymerization and coacervation; dissolving the active ingredient in a solution together with a polymer followed by solvent evaporation; by mixing the active ingredient with a wax or polymer (by mixing dry ingredients followed by melting the mixture or by mixing the active ingredient with a molten wax or polymer, followed by solidification of the mixture), then producing particles of the mixture by prilling, milling, extrusion, spray chilling, etc. The active ingredient generally represents between about 5% and about 50% of such a controlled-release formulation.

Salts of the compounds of the invention can be formulated and applied as aqueous solutions at a concentration of between about 0.05% to about 50% by weight and preferably from about 0.1% and about 10% by weight and applied to crops in this form. Such solutions can be prepared as concentrates that are diluted with an aqueous solvent or other appropriate solvent to the desired concentration for use. Such solutions optionally include a surface active agent and/or one or more auxiliary materials to increase the activity of the active ingredient, such as glycerin, methylethylcellulose, hydroxyethyl cellulose, polyoxyethylenesorbitan monooleate, polypropylene glycol, polyacrylic acid, polyethylene sodium malate, or polyethylene oxide, etc. Such auxiliary materials are generally present at a concentration of about 0.1% to about 5% by weight, preferably from about 0.5% to about 2% by weight of the solution. Such compositions can also optionally include an agronomically acceptable surfactant.

The compounds and formulations of the invention can be applied by conventional method, including, but not limited to, hydraulic sprays, aerial sprays, or dusts. For low-volume applications a solution of the compound is usually used. The optimum formulation, volume, concentration, application rate, timing of application (including stage of plant development), and method of application will depend on a variety of factors such as plant type, soil type, fertility, environmental factors, etc.

As used herein, the term "(gametocidally) effective amount" refers to an amount of a compound according to the present invention (or of a composition that comprises one or more compounds according to the present invention) that is sufficient to cause male sterility without commercially unacceptable phytotoxicity.

The Use of the Compounds of the Invention for Hybrid Seed Production

A hybrid is the first-generation seed produced by cross-pollination between two pure-line parents that are selected to have suitable flowering and agronomic characteristics for use in hybrid seed production. Hybrid seed is produced by planting the designated male and female parents in alternating strips. Male and female parents are selected based on long-term, known flowering history, with the male parent often selected to flower two to four days later than the female parent. It is important that adequate male pollen is available during the period that the female flowers are receptive. Plant lines and varieties for use as the male pollinators preferably have good anther extrusion and pollen-shed characteristics, and female parents preferably have good flower opening and female receptivity, under the environmental conditions existing in the production area. The timing of anthesis often depends upon temperature and pollen shed and on most plants usually begins early in the morning as soon as the temperature starts to increase. The flowering period is often shorter in hot, dry environments and longer under cool, humid conditions.

The female parent line is treated with a CHA of the present invention, which prevents these plants from producing pollen. Rows of treated female plants are planted sufficiently close (side-by-side or end-to-end) to strips of male pollinators to cause efficient cross pollination via wind-blown pollen. However, a gap is maintained between the male and female plots that is wide enough to permit CHA application to the female parent without significantly contacting the male parents and affecting pollen shed. This gap also allows for the harvest of the hybrid seed without significant mixing of seed produced by the male parent. The CHA is preferably applied uniformly to foliage of the female parent.

The following examples are included to demonstrate preferred embodiments of the invention. It should be appreciated by those of skill in the art that the techniques disclosed in the examples that follow represent techniques discovered by the inventors to function well in the practice of the invention and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Preparation of Compounds

Dialkyl [1-aryl or alkyl-hydroxy-1H-pyrazol-4-yl] phosphonates and related phosphonates with general structures 3, 4, 5, 7, 8, 10, 11 are prepared by the methods outlined in Schemes I–III.

Compounds with general structures 3 and 5 are prepared by condensation and subsequent cyclization under basic conditions of alkyl- or arylhydrazine hydrochloride salts with intermediate 2. For 1,2-dialkyl- or diarylhydrazine salts, compounds with general structure 5 are isolated in greater than 90% purity. For monoalkyl or arylhydrazine salts, compounds with general structure 3 are isolated in greater than 90% purity. Preparation of 2 is accomplished by methods to afford the product in quantitative yield (Katagiri et al., 1990. *Chem Lett*. 1855). Treatment of intermediate 2 with aryl- or alkylhydrazine hydrochloride salts in water at 120° C. followed by neutralization resulted in 1,4-C-addition to the $\alpha,\beta$-unsaturated $\pi$-system followed by elimination of water. The initial addition product is observed by high pressure liquid chromatography (HPLC) analysis. Addition of base then affected the cyclization to afford, after acidification, the phosphonopyrazole products. Before acidification, the aqueous phase is washed with organic solvents to remove impurities. This method is simpler as there is no purification step and can be performed with an aqueous solvent. In addition, the intermediates are stable at room temperature indefinitely. Moreover, this method is more efficient and higher yielding than similar published cyclocondensation reactions (Khotinen and Polozov, 1990. *Phosphorous, Sulfur Silicon Relat. Elem*. 83:53; Nifant'ev et al., 1977. *Khim. Geterotsikl. Soedin*., 513; Polozov et al., 1992. *Phosphorous, Sulfur Silicon Relat. Elem*., 73:153; Aboujaoude et al., 1985. *Tetrahedron* 41:427).

The reactions are carried out over a temperature range from ambient temperature to 160° C. in water or in organic solvents such as tetrahydrofuran (THF), dimethyformamide (DMF), dimethylsulfoxide (DMSO), acetonitrile, methanol, ethanol or other alcoholic solvents and mixtures of these solvents and water. Other bases such as hydroxides, alkoxides, hindered bases like lithium diisopropylamine (LDA), potassium or sodium hexamethyldisilamide (KHMDS, NaHMDS); non-nucleophilic strong bases such as sodium or lithium hydride (NaH, LiH) are also effective in this method. Aprotic organic solvents are required for bases that are not stable in protic solvents. For organic solvents, after cyclization and before acidification the solvent is removed and the crude mixture is dissolved in aqueous solvent, then washed with organic solvent.

Scheme I

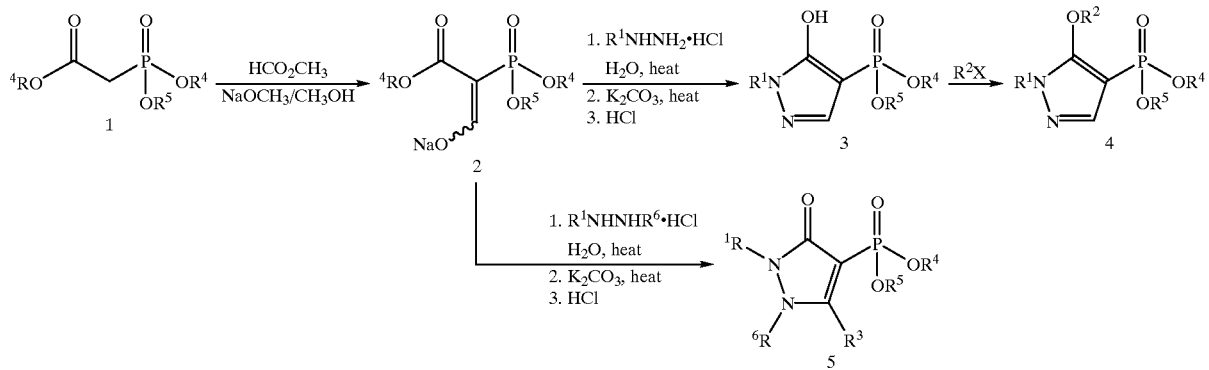

Compounds with general structure 7 are prepared by the method outlined in Scheme II. A slurry of aryl- or alkylhydrazine hydrochloride in anhydrous THF is cooled and treated with 2 equivalents of strong base (e.g., potassium t-butoxide or n-butyllithium) dissolved in THF. After several minutes, methyl (E and Z)-2-(dimethoxyphosphoryl)-3-methoxy-2-propenoate (structure 6) dissolved in anhydrous THF is added. The cooled mixture is stirred for five minutes, allowed to warm to room temperature, then treated with excess aqueous HCl. The product is extracted with organic solvent and concentrated. The crude products (structure 7), are purified by silica gel chromatography.

Scheme II

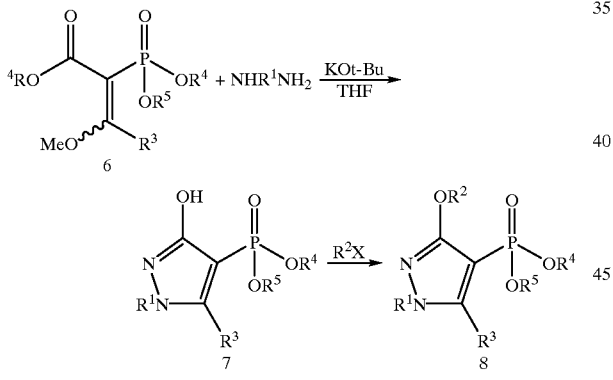

Compounds with general structure 10 are prepared by the method shown in Scheme III. The dimethoxyphosphinyl methyl ester (structure 9), is suspended in water. The aryl or alkylhydrazine hydrochloride is added, and the mixture is stirred with heating for several hours. Addition of base then affected the cyclization to afford, after acidification, the phosphonopyrazole products, structure 10. The crude products are purified by radial chromatography (silica).

Scheme III

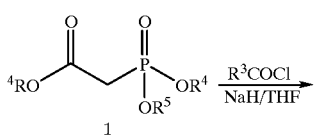

-continued

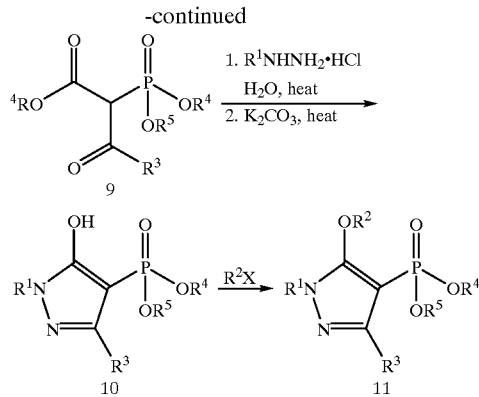

Compounds with general structure 3, 7 and 10 can exist in keto or enol tautomeric forms as indicated below. Compounds with general structure 3, 7 and 10 can be alkylated at oxygen by treatment with base followed by addition of alkyl or benzylhalide or by other established methods to afford compounds of general structure 4, 8 and 11.

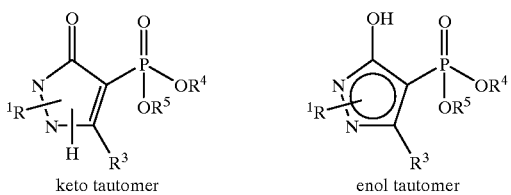

keto tautomer             enol tautomer

General Structures: Keto and enol tautomers of compounds with general structure 3, 7 and 10.

Compounds with general structure 3, 4, 5, 7, 8, 10, and 11 are hydrolyzed at phosphorus to give the mono alkyl phosphonate esters by treatment with 5–50% aqueous NaOH or by other established methods. Compounds with general structure 3, 4, 5, 7, 8, 10, and 11 are hydrolyzed at phosphorus to give the phosphonic acids by treatment with treatment with tetramethylsilyliodide (TMSI) or tetramethylsilylbromide (TMSBr) in methylene chloride or by other established methods. The mono alkyl phosphonate esters and phosphonic acids are converted to the potassium or sodium salts by treatment with potassium or sodium alkoxides in methanol or by other established procedures. Products are characterized by $^1H$, $^{13}C$, $^{31}P$ NMR spectroscopy and elemental analysis.

Method A. General Procedure for the Preparation of Dialkyl [1-aryl or alkyl-5-hydroxy-1H-pyrazol-4-yl]phosphonates (compounds of structure 3).

A 100 mL 1-necked round-bottomed flask is charged with 3-sodium alkoxy-2-dimethylphosphonoacrylate (structure 2, 9.0 mmol) and an arylhydrazine hydrochloride (9.9 mmol, 1.1 eq.) dissolved in $H_2O$ (50 mL). The mixture is heated in a 120° C. oil bath with stirring under an atmosphere of $N_2$. After 5–10 minutes of heating, thin layer chromatography (TLC) (15% IPA/85% EtOAc) and HPLC (Hewlett Packard Series 1100 system using a Hewlett Packard ODS hypersil column, 5 μm 100×4.6 mm) indicated complete conversion to the intermediate adduct. The flask is removed from the oil bath and $K_2CO_3$ (9.9 mmol, 1.1 equivalent) is added, and the mixture is again heated in a 120° C. oil bath with stirring under an atmosphere of $N_2$ for 5–10 minutes or until TLC and HPLC indicated the cyclization is complete. The mixture is cooled to room temperature and washed with EtOAc (2×30 mL). The aqueous phase is acidified with concentrated HCl and the product extracted with EtOAc (3×30 mL). The combined organic extracts are dried ($MgSO_4$), filtered and concentrated in vacuo to afford the product as a yellow solid. The crude products of structure 3 are of analytical purity. Crude products of structure 5 required preparative chromatographic purification (Waters Delta Prep 3000 series chromatograph using a Dynamax 60A C18 83–221-C column).

This method is also applied to alkyl and benzylhydrazine hydrochloride salts; however, in these cases, both the 3- and 5-isomers are isolated and chromatographic purification is required (same system as used for structure 5). The isomeric mixtures result, presumably, from the comparable nucleophilicity of the hydrazine nitrogens. The following compounds are produced by Method A.

Dimethyl [1-(4-chlorophenyl)-5-hydroxy-1H-pyrazol-4-yl]phosphonate (compound 3a). The reaction is carried out using 8.8 mmol of compound 2 to afford the product as a yellow solid (1.9 g, 6.3 mmol, 78%): $^1H$ NMR (400 MHz, $CDCl_3$) δ 7.77 (d, J=8.9 Hz, 2H), 7.54 (s, 1H), 7.43 (d, J=8.9 Hz, 1H ), 3.78 (d, J=11.8 Hz, 6H); $^{13}C$ NMR (100 MHz, $CDCl_3$) δ 158.9 (d, J=22.1 Hz), 139.8 (d, J=10.7 Hz), 136.2, 132.5, 129.2, 122.6, 83.8 (d, J=220.5 Hz), 53.0 (d, J=5.0 Hz)); $^{31}P$ NMR (162 MHz, $CDCl_3$) δ 19.81. Analytical calculated for $C_{11}H_{12}ClN_2O_4P$: C, 43.71; H, 4.00; N, 9.27; . Found: C, 43.71; H, 3.95; N, 9.20.

Dimethyl [1-(4-fluorophenyl)-5-hydroxy-1H-pyrazol-4-yl]phosphonate (compound 3b). The reaction is carried out using 4.4 mmol of compound 2 to afford the product as a pale yellow solid (0.87 g, 3.0 mmol, 70%): $^1H$ NMR (400 MHz, $CDCl_3$) δ 8.67 (bs, 1H), 7.76 (dd, J=9.0, 4.7 Hz, 2H), 7.54 (s, 1H), 7.15 (t, J=8.6 Hz, 2H), 3.78 (d, J=11.8 Hz, 6H); $^{13}C$ NMR (100 MHz, $CDCl_3$) δ 161.2 (d, J=247.2 Hz), 158.7 (d, J=22.1 Hz), 139.7 (d, J=10.3 Hz), 133.7, 123.5 (d, J=8.8 Hz), 115.9(d, J=22.9 Hz), 83.6 (d, J=220.9 Hz), 53.0 (d, J=5.0 Hz); $^{31}P$ NMR (162 MHz, $CDCl_3$) d 19.85; $^{19}F$ NMR (376 MHz, $CD_3OD$) δ -114.99 (heptet, J=4.3 Hz). Analytical calculated for $C_{11}H_{12}FN_2O_4P$: C, 46.15; H, 4.23; N, 9.79. Found: C, 45.60; H, 4.33; N, 9.36.

Dimethiyl [1-(2-chlorophenyl)-5-hydroxy-1H-pyrazol-4-yl]phosphonate (compouwd 3c). The reaction is carried out using 4.7 mmol of compound 2 to afford the product as a pale yellow solid (0.82 g, 2.7 mmol, 58%): $^1H$ NMR (400 MHz, $CDCl_3$) δ 9.20 (bs, 1H), 7.59 (s, 1H), 7.55–7.39 (m, 4H), 3.78 (d, J=11.8 Hz, 6H); $^{13}C$ NMR (100 MHz, $CDCl_3$) δ 159.8 (d, J=21.4 Hz), 140.4 (d, J=11.1 Hz), 134.3, 132.1, 130.7, 130.4, 129.3, 127.5, 82.6 (d, J=222.4 Hz), 53.0 (d, J=5.3 Hz); $^{31}P$ NMR (162 MHz, $CDCl_3$) δ 19.80. Analytical calculated for $C_{11}H_{12}ClN_2O_4P$: C, 43.71; H, 4.00; N, 9.27; . Found: C, 43.23; H, 4.19; N, 8.93.

Dimethyl [1-(4-bromophenyl)-5-hydroxy-1H-pyrazol-4-yl]phosphonate (compound 3d). The reaction is carried out using 4.4 mmol of compound 2 to afford the product as a pale yellow solid (1.05 g, 3.0 mmol, 70%): $^1H$ NMR (400 MHz, $CDCl_3$) δ 9.40 (bs, 1H), 7.72 (d, J=9.1 Hz, 2H), 7.58 (d, J=8.9 Hz, 2H), 7.54 (d, J=0.5 Hz, 1H), 3.77 (d, J=11.6 Hz, 6H); $^{13}C$ NMR (100 MHz, $CDCl_3$) δ 159.0 (d, J=22.1 Hz), 139.9 (d, J=10.7 Hz), 136.7, 132.1, 122.9, 120.4, 83.8 (d, J=220.9 Hz), 53.0 (d, J=5.3 Hz); $^{31}P$ NMR (162 MHz, $CDCl_3$) δ 19.73. Analytical calculated for $C_{11}H_{12}BrN_2O_4P$: C, 38.15; H, 3.50; N, 8.09. Found: C, 37.82; H, 3.66; N, 7.70.

Dimethyl [1-cyclohexyl-5-hydroxy-1H-pyrazol-4-yl] phosphonate (compound 3e). The reaction is carried out using 4.7 mmol of compound 2 to afford a mixture of the 3- and 5-hydroxy isomers (1.2:1.0, 22%). The 5-hydroxy product (F15–17) was purified by reverse phase chromatography ($CH_3CN:H_2O$, 10:90; to 40:60 over 20 min; to 100:0 over 5 min; Note: all solvents contained 0.1% trifluoroacetic acid (TFA)) and was isolated as a white solid (0.07 g, 0.26 mmol, 6%): $^1H$ NMR (400 MHz, $CDCl_3$) δ 11.45 (bs, 2H), 7.54 (s, 1H), 4.20 (m, 1H), 3.75 (d, J=11.8 Hz, 6H), 1.96–1.71 (m, 7H), 1.41–1.24 (m, 3H); $^{13}C$ NMR (100 MHz, $CDCl_3$) δ 157.5 (d, J=21.2 Hz), 138.6 (d, J=12.6 Hz), 82.6 (d, J=225.8 Hz), 56.5, 53.2 (d, J=5.3 Hz), 31.6, 25.5, 25.0; $^{31}P$ NMR (162 MHz, $CDCl_3$) δ 19.23. Analytical calculated for $C_{11}H_{19}N_2O_4P$: C, 48.16; H, 6.99; N, 10.22. Found: C, 46.15; H, 6.66; N, 9.30.

Method B. General Procedure for the Preparation of Dialkyl [1-aryl or alkyl-5-hydroxy-1H-pyrazol-4-yl]phosphonates (compounds of structure 3).

A mixture of trimethylphosphonoacetate (13.4 g, 0.073 mol), N,N-dimethylformamide dimethyl acetal (13.2 g, 0.11 mol), and methanol (10 mL) is heated and held at reflux for 18 hours. The cool mixture is concentrated in vacuo to give trimethyl (dimethylaminomethylene) phosphonoacetate as light yellow solids/oil (22.4 g, 129%). A mixture of crude dimethylaminomethylene intermediate (7.8 g, 0.032 mol), 4-chlorophenylhydrazine hydrochloride (5.8 g, 0.032 mol), and methanol (40 mL) is heated and held at reflux under nitrogen for one hour. Thin layer chromatography (TLC) (EtOAc) of an aliquot shows that the trimethyl (dimethylaminomethylene) phosphonoacetate is consumed. After cooling to 45° C., water (15 mL) is added, followed by potassium carbonate (4.5 g, 0.032 mol). This mixture is heated and held at reflux for thirty minutes. TLC of an aliquot shows complete conversion to product. The reaction mixture was cooled to 25° C., and was worked up as described in Method A, to give compound 3a (6.20 g, 64%) as a dark amber solid. $^1H$ and $^{31}P$ NMR spectra indicated pure product.

Method C. General Procedure for the Preparation of Dialkyl [1-aryl or alkyl-5-hydroxy-1H-pyrazol-4-yl]phosphonates (compounds of structure 3).

To a slurry of methyl 3-oxy-2-dimethylphosphonoacrylate sodium salt (4.1 g, 0.017 mol) in anhydrous DMSO (25 mL) under nitrogen is added methyl iodide (4.5 g, 0.031 mol), and the reaction mixture stirred for 18 hours at ambient temperature. The mixture is poured into dilute sodium chloride solution and extracted with $CH_2Cl_2$ (6×75 mL). The extracts are washed with water (100 mL), dried ($MgSO_4$), filtered and concentrated in vacuo to afford a brown oil (5.5 g). Partial separation by chromatography on silica gel (EtOAc) of half the crude product afforded pure E-isomer (0.27 g); a mixture of the E- and Z-isomers (0.75 g); and pure Z-isomer (0.14 g). The E- and Z-products are isolated in 52% overall yield. Methyl (E)-2-(dimethoxyphosphoryl)-3-methoxy-2-propenoate (E-isomer). $^1$H NMR (300 MHz, CDCl$_3$): δ 7.55 (d, J$_{H-P}$=10.8 Hz, 1H), 4.06 (s, 3H), 3.78 (d, J$_{H-P}$=2.7 Hz, 6H), 3.75 (s, 3H). $^{31}$P NMR (121 MHz, CDCl$_3$) δ 20.74. Methyl (Z)-2-(dimethoxyphosphoryl)-3-methoxy-2-propenoate (Z-isomer). $^1$H NMR (300 MHz, CDCl$_3$) δ 7.90 (d, J$_{H-P}$=31.8 Hz, 1H), 4.03 (s, 3H), 3.78 (d, J$_{H-P}$=5.1 Hz, 6H), 3.75 (s, 3H). $^{31}$P NMR (121 MHz, CDCl$_3$) δ 15.50. A mixture of crude methyl-2-(dimethoxyphosphoryl)-3-methoxy-2-propenoate (6.9 g, 0.030 mol), 4-chlorophenylhydrazine hydrochloride (5.4 g, 0.030 mol), and methanol (40 mL) is heated and held at reflux under nitrogen for one hour. TLC (EtOAc) of an aliquot shows that the methyl-2-(dimethoxyphosphoryl)-3-methoxy-2-propenoate is consumed. After cooling to 45° C., water (15 mL) is added, followed by potassium carbonate (4.1 g, 0.030 mol). This mixture is heated and held at 65° C. for one hour. TLC of an aliquot shows complete conversion to product. The reaction mixture is cooled to 25° C., and further worked up as described for Method A, to afford compound 3a as a red-amber solid (5.90 g, 65%). $^1$H and $^{31}$P NMR spectra indicated 90% assay product, which results in a net 58% yield.

Selected compounds are prepared by Methods A, B, C, and by the methods described in reactions (Khotinen and Polozov, 1990. *Phosphorous, Sulfur Silicon Relat. Elem.* 83:53; Polozov et al. 1992. *Phosphorous, Sulfur Silicon Relat. Elem.*, 73:153). These are merely representative compounds prepared by these methods for relative yield comparison. Table 1 demonstrates that the yield of product by Method A was generally greater than Method B, which was generally greater than Method C, which was generally greater than the method described by Khotinen and Polozov (1990. *Phosphorous, Sulfur Silicon Relat. Elem.* 83:53) and by Polozov et al. (1992. *Phosphorous, Sulfur Silicon Relat. Elem.*, 73:153).

TABLE 1

Comparative Yields for Selected Compounds of group 3 by the methods of A, B, C and procedures described by Khotinen and Polozov or by Polozov.

| Compound | Ar | Yield (%)[a] | Method |
| --- | --- | --- | --- |
| 3d | 4-ClPh | 78 | A |
|  |  | 64 | B |
|  |  | 58 | C |
| 3a | Ph | 79 | A |
|  |  | 34 | Khotinen; Polozov |
| 3j | 4-NO$_2$Ph | 79 | A |
|  |  | 31 | Khotinen; Polozov |

[a]Overall yield including preparation of intermediates.

General Procedure for the Preparation of Dimethyl (1-Aryl-3-alkyl or aryl-5-hydroxy-1H-pyrazol-4-yl)phosphonates (compounds of structure 10).

The dimethoxyphosphinyl methyl ester (1–2.5 mmol) is suspended in water. The phenylhydrazine hydrochloride (1–2.5 mmol) is added, and the mixture is stirred at 110° C. for 2 h. The reaction is cooled and K$_2$CO$_3$ (2 eq.) is added. The reaction is stirred at 110° C. for 2 h, cooled to room temperature and stirred for an additional 16 h. The reaction mixture is washed with ether, acidified to pH=2 with 0.5N HCl, and extracted with EtOAc (3×50 mL). The combined extracts are washed with NaCl (sat.), dried (Na$_2$SO$_4$), filtered, and concentrated to an oil. A portion of this material is purified by radial chromatography (silica) with EtOAc or mixtures of hexane:isopropanol (90–95%) or hexane:EtOAc (90–95%) to give the desired products.

Dimethyl [1-(4-chlorophenyl)-5-hydroxy-3-phenyl-1H-pyrazol-4-yl]phosphonate (compound 10a). This reaction is carried out with compound 9 (0.71 g, 2.5 mmol) and 4-Cl-phenylhydrazine. HCl (0.49 g, 2.75 mmol) to yield crude product (0.81 g, 85%). Crude material (0.75 g) is separated twice by radial chromatography (silica) with EtOAc to afford pure product (0.40 g, 45.3%). $^1$H NMR (300 MHz, CDCl$_3$) δ 11.42 (bs, 1H), 7.95–7.90 (m, 4H), 7.47–7.44 (m, 5H), 3.76 (d, J=12.0 Hz, 6H). $^{13}$C NMR (75 MHz, CDCl$_3$) δ 161.0 (d, J=22.9 Hz), 151.4 (d, J=9.4 Hz), 136.5, 132.4, 132.2, 129.2, 129.2, 128.7, 127.2, 122.7, 80.8 (d, J=215.2 Hz), 53.1 (d, J=4.6 Hz). $^{31}$P NMR (121 MHz, CDCl$_3$) δ 21.93. Analytical calculated for C$_{17}$H$_{16}$N$_2$O$_4$PCl: C, 53.90; H, 4.27; N, 7.40; Cl, 9.36. Found: C, 55.62; H, 4.35; N, 7.58; Cl, 9.99.

Dimethyl[1-(3,5-dimethylphenyl)-5-hydroxy-3-phenyl-1H-pyrazol-4-yl]phosphonate (compound 10b). This reaction was carried out with compound 9 (0.71 g, 2.5 mmol) and 3,5 dimethylphenylhydrazine. HCl (0.43 g, 2.50 mmol) to yield crude product (0.65 g, 69.8%). Crude material (0.60 g) is separated 4 times by radial chromatography (silica) with mixtures of hexane: EtOAc or hexane: isopropanol to afford pure product (0.10 g, 11.7%). $^1$H NMR (300 MHz, CDCl$_3$) δ 11.24 (bs, 1H), 7.95 (d, J=1.8 Hz, 1H), 7.92 (d, J=1.5 Hz, 1H), 7.52 (s, 2H), 7.50–7.40 (m, 3H), 7.00 (s, 1H), 3.76 (d, J=12.0 Hz, 6H), 2.42 (s, 6H). $^{13}$C NMR (75 MHz, CDCl$_3$) δ 160.8 (d, J=22.9 Hz), 151.1 (d, J=9.4 Hz), 138.9, 137.6, 132.5, 129.0, 128.9, 128.6, 127.2, 119.8, 80.2 (d, J=215.2 Hz), 53.0 (d, J=4.6 Hz), 21.5. $^{31}$P NMR (121 MHz, CDCl$_3$) δ 21.31. Analytical calculated for C$_{19}$H$_{21}$N$_2$O$_4$P: C, 61.28; H, 5.70; N, 7.52. Found: C, 62.37; H, 5.75; N, 7.67.

General Procedure for the Alkylation of Dialkyl [2-aryl or alkyl-3-hydroxy-1H-pyrazol-4-yl]phosphonates.

To a solution of 1.65 mmole (1 equiv.) hydroxypyrazol-4-yl phosphonate in 20 mL anhydrous DMF cooled to 0° C. is added 1.1 equiv. of NaH (60% in oil dispersion). The mixture is stirred for 15–20 min. The appropriate electrophile (1.1 eq.) is added, followed by gentle warming to room temperature. The reaction is stirred for 18 hours at 30° C., poured onto 50–100 mL of ice water and diluted with ethyl acetate. The organic layer is washed with ethyl acetate (3×50 mL). The ethyl acetate layers are combined, dried (MgSO$_4$) and concentrated in vacuo. Excess DMF is removed by Kugelrohr distillation (75° C./0.2 mm Hg) followed by silica gel chromatography (2% IPA initially, increasing to 10% IPA in hexanes).

Dimethyl{1-(4-Chlorophenyl)-5-[(4-chlorobenzyl)oxy]-1H-pyrazol-4-yl}phosphonate (compound 4a). The reaction is carried out using 0.207 mmol of dimethyl [2-(4-chlorophenyl)-3-hydroxy-1H-pyrazol-4-yl]phosphonate to afford a light tan oil. The crude product is purified by reverse phase chromatography (CH$_3$CN:H$_2$O (0.5% TFA); 20:80 to 100% over 20 min.) to afford the product as a tan solid (12.5 mg, 0.031 mmol, 15%): $^1$H NMR (400 MHz, CD$_3$OD) δ 7.68 (s, 1H), 7.46 (d, J=8.6 Hz, 2H), 7.36 (d, J=8.9 Hz, 2H), 7.30 (d, J=8.6 Hz, 2H), 7.18 (m, 2H), 5.38 (s, 2H); $^{31}$P NMR (162 MHz, CD$_3$OD) δ 9.14.

Dimethyl{1-(4-chlorophenyl)-5-[(2-nitrobenzyl)oxy]-1H-pyrazol-4-yl}phosphoizate (compound 4b). The reaction is carried out using 2.02 mmol of dimethyl [2-(4-chlorophenyl)-3-hydroxy-1H-pyrazol-4-yl]phosphonate to afford a brown oil. The crude product is purified by removing excess DMF using Kügelrohr distillation at 50° C./0.2 mm Hg followed by radial chromatography (IPA:ETOAc; 5:95) to afford the product as a tan solid (426.8 mg, 0.98 mmol, 48%): $^1$H NMR (400 MHz, CDCl$_3$) δ 8.10 (dd, J=8.9, 1.0 Hz, 1H), 7.76 (d, J=1.4 Hz, 1H), 7.65 (m, 2H), 7.54 (d, J=9.1 Hz, 2H), 7.51 (m, 1H), 7.39 (d, J=9.0, 2H), 5.87 (s, 2H), 3.60 (d, J=11.5 Hz, 6H); $^{13}$C NMR (100 MHz, CDCl$_3$) δ 156.0 d 156.1 (d, J=8.5 Hz), 147.7, 144.1 (d, J=20.5 Hz), 136.0, 134.1, 133.8, 131.6, 129.3, 129.3, 129.1, 125.2, 124.8, 92.5 (d, J=200.0 Hz), 73.9, 52.9 (d, J=7.5 Hz); $^{31}$P NMR (162 MHz, CDCl$_3$) δ 15.61.

General Procedure for the Preparation of Monoalkyl Phosphonates.

The dialkyl phosponate is suspended in 10% NaOH solution (40–50 mL) in a 100 mL one-necked round-bottomed flask with stirring. The mixture is heated in an oil bath (80–100° C.) for 2–6 hours or until TLC (IPA:hexane; 15:85) indicates the starting phosphonate has been consumed. The reaction is cooled to room temperature, acidified with concentrated HCl and the product extracted with EtOAc (3×30 mL). The combined organic extracts are dried (MgSO$_4$), filtered and concentrated in vacuo to afford the product as an off-white solid.

Hydrogen methyl [2-(3,5-dimethylphenyl)-3-hydroxy-1H-pyrazol-4-yl]phosphonate (compound 3g). The reaction is carried out using 2.4 mmol of the dimethyl phosphonate to afford the product as a off-white solid (640 mg, 2.3 mmol, 95%): $^1$H NMR (400 MHz, CD$_3$OD) δ 7.71 (s, 1H), 7.24 (s, 2H), 7.03 (s, 1H), 3.70 (d, J=11.5 Hz, 3H); $^{13}$C NMR (100 MHz, CD$_3$OD) δ 156.4 (d, J=19.6 Hz), 140.2 (d, J=12.6 Hz), 138.0, 135.7, 128.0, 119.5, 50.7 (d, J=5.0 Hz), 19.1; $^{31}$P NMR (162 MHz, CD$_3$OD) δ 14.80.

Hydrogen methyl [2-(4-chlorophenyl)-3-hydroxy-1H-pyrazol-4-yl]phosphonate (compound 3h). The reaction is carried out using 1.8 mmol of the dimethyl phosphonate to afford the product as a off-white solid (500 mg, 1.7 mmol, 94%): $^1$H NMR (400 MHz, CD$_3$OD) δ 7.72 (s, 1H), 7.69 (d, J=8.9 Hz, 2H), 7.50 (d, J=8.9 Hz, 2H), 3.79 (d, J=11.8 Hz, 3H); $^{31}$P NMR (162 MHz, CD$_3$OD) δ 14.43.

General Procedure for the Preparation of Phosphonic Acids.

A 50 mL one-necked round-bottomed flask is charged with a dimethyl phosphonate dissolved in CH$_2$Cl$_2$ (30 mL). To the stirred solution is added TMSI (4 eq.) and the resulting solution is stirred at room temperature until TLC (IPA:hexane; 15:85) indicates the phosphonate is consumed (1–3 h). The solvent is removed in vacuo, methanol (30 mL) is added to the residue and the resulting solution is stirred for 20 min. The methanol is removed in vacuo, and fresh methanol is added and stirred for 10 min. The methanol is removed in vacuo to afford an orange-red oil. This residue is dissolved in minimal methanol (1–2 mL) and then diluted with CH$_2$Cl$_2$ (30 mL). The product precipitated from the solution as a white solid upon dilution with CH$_2$Cl$_2$. The mixture is cooled in a refrigerator overnight and the product is isolated by filtration.

2-(4-Chlorophenyl)-3-[(2-nitrobenzyl)oxy]-1H-pyrazol-4-yl phosphonic acid (compound 4c). The reaction is carried out using 0.217 mmol of structure 3 to afford a light tan oil. The crude product is purified by reverse phase chromatography (CH$_3$CN:H$_2$O (5% TFA); 20:80 to 100% CH$_3$CN over 20 min.) to afford the product as a tan solid (50 mg, 0.12 mmol, 56%): $^1$H NMR (400 MHz, CD$_3$OD) δ 8.00 (d, J=2.3 Hz, 1H), 7.68 (m, 1H), 7.64 (m, 2H), 7.52 (m, 1H), 7.44 (m, 2H), 7.36 (d, J=8.6 Hz, 2H) 5.80 (s, 2H); $^{31}$P NMR (162 MHz, CD$_3$OD) δ 9.17.

2-(4-Chlorophenyl)-3-hydroxy-1H-pyrazol-4-yl phosphonic acid (compound 3j). The reaction is carried out using 1.7 mmol of structure 1 to afford the product as a off-white solid (424 mg, 1.6 mmol, 92%): $^1$H NMR (400 MHz, CD$_3$OD) δ 7.70 (d, J=7.0 Hz, 2H), 7.67 (s, 1H), 7.49 (d, J=7.0 Hz, 2H); $^{31}$P NMR (162 MHz, CD$_3$OD) δ 11.61.

2-(3,5-Dimethylphenyl)-3-hydroxy-1H-pyrazol-4-yl phosphonic acid (compound 3k). The reaction is carried out using 2.4 mmol of dimethyl [2-(3,5-dimethylphenyl)-3-hydroxy-1H-pyrazol-4-yl]phosphonate to afford the product as the HI salt (940 mg, 2.4 mmol, 100%). The salt (1.7 mmol) is neutralized by dissolving in minimal MeOH (1–2 mL) followed by dilution with CH$_2$Cl$_2$ (20–30 mL). To the homogeneous solution is added propylene oxide (2 eq.) with stirring. After 5 min, the product precipitated from the solution and is isolated as an off-white solid (445 mg, 1.7 mmol, 100%): $^1$H NMR (400 MHz, CD$_3$OD) δ 7.66 (s, 1H), 7.25 (s, 2H), 7.02 (s, 1H); $^{13}$C NMR (100 MHz, CD$_3$OD) δ 158.1 (d, J=19.5 Hz), 141.9(d, J=13.4 Hz), 140.2, 138.2, 130.0, 121.5, 93.8 (d, J=217.4 Hz), 21.4; $^{31}$P NMR (162 MHz, CD$_3$OD) δ 11.84.

General Procedure for the Preparation of Potassium Salts (compounds of the structure 3l, 3m, and 3n).

The phosphonic acid (1 equivalent) is suspended in methanol (MeOH, 5 mL/100 mg) in a round-bottomed flask with stirring. To the suspension is added KOH solution (1.0 equiv., 5 mg/mL in MeOH) and the mixture is stirred at room temperature for 0.5–2 hours. The solvent is removed in vacuo to afford the potassium salt as an off-white or white solid.

General Procedures for the Preparation of Dimethyl (1-aryl-3-hydroxy-1H-pyrazol-4-yl)phosphonates (compounds of structure 8).

Method I: A slurry of phenyl hydrazine hydrochloride (4.4 mmol) in anhydrous THF (25 mL) cooled in an ice bath is treated with potassium t-butoxide in THF (10 mmol 1.0 M). After 5 minutes, methyl (E and Z)-2-(dimethoxyphosphoryl)-3-methoxy-2-propenoate (MX 3128-F12/G1, 4.4 mmol) in anhydrous THF (2 mL) is added. The mixture is stirred 5 minutes in an ice bath, allowed to warm to room temperature over 1–2 hours, then treated with excess 1% aqueous HCl. The product is extracted with CH$_2$Cl$_2$(3×75 mL), and the extracts dried (MgSO$_4$), filtered and concentrated in vacuo. Purification by silica gel chromatography (IPA/hexanes 15/85) afforded the desired product.

Method II: A slurry of phenyl hydrazine hydrochloride (4.4 mmol) in anhydrous THF (35 mL) cooled to −15° C. is treated with n-butyl lithium in hexanes (10 mmol, 2.5 M). After 5 minutes, methyl (E and Z)-2-(dimethoxyphosphoryl)-3-methoxy-2-propenoate (4.4 mmol) in anhydrous THF (2 mL) is added. The mixture is stirred 5 minutes in at −15° C., allowed to warm to room temperature over 1–2 hours, then treated with excess 1% aqueous HCl. The product is extracted with CH$_2$Cl$_2$(3×75 mL), and the extracts dried (MgSO$_4$), filtered and concentrated in vacuo. Purification by silica gel chromatography (IPA/hexanes 15/85) afforded the desired product.

Dimethyl [1-(4-bromophenyl)-3-hydroxy-1H-pyrazol-4-yl]phosphonate (compound 8a). Method I is carried out using 4.9 mmol of 4-bromophenyl hydrazine hydrochloride to afford the product as a red-brown oil (0.56 g, 1.3 mmol, 27%). $^1$H NMR (300 MHz, CDCl$_3$) δ 8.07 (d, J$_{H-P}$=2.4 Hz, 1H), 7.52 (d, J=9.3 Hz, 2H), 7.42 (d, J=9.0 Hz, 2H), 3.82 (d, J$_{H-P}$=11.4 Hz, 6H); $^{13}$C NMR (75 MHz, CDCl$_3$) δ 164.9 (d, J$_{C-P}$=9.3 Hz), 137.9, 132.7, 132.3 (d, J$_{C-P}$=21.3 Hz), 120.6, 120.4, 92.5 (d, J$_{C-P}$=219.0 Hz), 53.1 (d, J$_{C-P}$=5.4 Hz); $^{31}$P NMR (121 MHz, CDCl$_3$) δ 16.96. Analytical calculated for C$_{11}$H$_{12}$BrN$_2$O$_4$P: C, 38.06; H, 3.48; N, 8.07. Found: C, 36.96; H, 3.52; N, 7.56.

General Procedure for the Preparation of 4-Dimethoxy Phosphonyl-1-aryl-2-alkyl-3-pyrazolin-5-ones (compounds of structure 5).

A 100 mL 1-necked round-bottomed flask is charged with an arylhydrazine hydrochloride (2.6 mmol, 1.2 equivalent) dissolved in $H_2O$:MeOH (1:1, 10 mL). The mixture is heated in a 120° C. oil bath with stirring. 3-Sodium alkoxy-2-dimethylphosphonoacrylate (structure 2, 2.1 mmol, 1.0 equivalent) is dissolved in $H_2O$:MeOH (1:1, 5 mL) and is added to the hot arylhydrazine solution. The reaction is monitored by reverse phase chromatography ($CH_3CN$:$H_2O$, 20:80; to 100:0 over 20 min; Note: all solvents contained 0.1% TFA) and after 30–45 min of heating, indicated complete conversion to the intermediate adduct. The flask is removed from the oil bath, and $K_2CO_3$ (9.9 mmol, 2.1 eq.) is added and the mixture is again heated in a 120° C. oil bath with stirring for 30–60 min or until HPLC indicated the cyclization is complete. The mixture is cooled to room temperature and is extracted with EtOAc (3×40 mL). The combined organic extracts are dried ($MgSO_4$), filtered and concentrated in vacuo to afford the crude product as a yellow solid. The crude products are purified by radial chromatography (TLC (IPA:EtOAc; 2:8) to afford the products as off-white solids.

Dimethyl [2-(4-chlorophenyl)-2,3-dihydro-1-ethyl-3-oxo-pyrazol-4-yl]phosphonate (compound 5a). The reaction is carried out using 1.5 mmol of structure 2 to afford the crude product as a pale yellow oil (260 mg, 0.8 mmol, 53%). Over time, white crystals formed in the oil. The crystals are collected and washed with cold EtOAc: $^1H$ NMR (400 MHz, $CDCl_3$) δ 8.00 (d, J=4.8 Hz, 1H), 7.47 (d, J=8.6 Hz, 2H), 7.29 (d, J=8.9 Hz, 2H), 3.84 (d, J=11.5 Hz, 6H), 3.73 (q, J=7.2 Hz, 2H), 1.18 (t, J=7.2 Hz, 3H); $^{13}C$ NMR (100 MHz, $CDCl_3$) δ 163.8 (d, J=14.1 Hz), 148.4 (d, J=18.7 Hz), 134.1, 131.7, 129.7, 126.8, 95.3 (d, J=223.5 Hz), 53.0 (d, J=5.7 Hz), 45.6, 13.0; $^{31}P$ NMR (162 MHz, $CDCl_3$) δ 15.27. Analytical calculated for $C_{13}H_{16}ClN_2O_4P$: C, 47.27; H, 4.89; N, 8.49. Found: C, 47.12; H, 4.90; N, 8.40.

Dimethyl[2-(4-chlorophenyl)-1-cyclohexyl-2,3-dihydro-3-oxo-pyrazol-4-yl]phosphonate (compound 5b). The reaction is carried out using 1.9 mmol of structure 2 to afford the crude product as a pale yellow oil (480 mg, 1.3 mmol, 64%). The crude product is purified by radial chromatography (IPA:EtOAc; 2:8) to afford the product as an off-white solid (190 mg, 0.5 mmol, 26%): $^1H$ NMR (400 MHz, $CDCl_3$) δ 8.06 (d, J=4.8 Hz, 1H), 7.47 (d, J=8.6 Hz, 2H), 7.23 (d, J=8.6 Hz, 2H), 3.83 (d, J=11.6 Hz, 6H), 3.56 (m, 1H), 2.03 (d, J=11.3 Hz, 2H), 1.84 (d, J=12.1 Hz, 2H), 1.68 (d, J=8.3 Hz, 1H), 1.40 (q, J=12.0 Hz, 2H), 1.17 (m, 3H); $^{13}C$ NMR (100 MHz, $CDCl_3$) δ 164.1 (d, J=14.1 Hz), 146.5 (d, J=19.1 Hz), 133.9, 132.2, 129.7, 126.8, 94.9 (d, J=223.2 Hz), 59.6, 53.0 (d, J=5.7 Hz), 31.2, 25.04, 24.99; $^{31}P$ NMR (162 MHz, $CDCl_3$) δ 15.62. Analytical calculated for $C_{17}H_{22}ClN_2O_4P$: C, 53.11; H, 5.77; N, 7.29. Found: C, 52.46; H, 5.77; N, 7.10.

Dimethyl[2-(3,5-dimethylphenyl)-2,3-dihydro-1-ethyl-3-oxo-pyrazol-4-yl]phosphonate (compound 5c). The arylhydrazine in this example is 89% pure as judged by $^1H$ NMR spectroscopy. The yield is calculated based on the amount of arylhydrazine; however, the amount of other reagents is based on the total weight of arylhydrazine plus impurities. The reaction is carried out using 3.0 mmol of structure 2 to afford the crude product as a pale yellow oil (510 mg, 1.6 mmol, 63%). The crude product is purified by radial chromatography (IPA:EtOAc; 2:8) to afford the product as an off-white solid (190 mg, 0.6 mmol, 23%): $^1H$ NMR (400 MHz, $CDCl_3$) δ 7.95 (d, J=4.6 Hz, 1H), 7.03 (s, 1H), 6.94 (s, 2H), 3.84 (d, J=11.6 Hz, 6H), 3.72 (q, J=7.2 Hz, 2H), 2.35 (s, 6H), 1.19 (t, J=7.3 Hz, 3H); $^{13}C$ NMR (100 MHz, $CDCl_3$) δ 163.8 (d, J=13.7 Hz), 146.6 (d, J=19.1 Hz), 139.4, 132.8, 130.3, 123.8, 94.2 (d, J=222.4 Hz), 53.5 (d, J=5.7 Hz), 45.3, 21.2, 13.2; $^{31}P$ NMR (162 MHz, $CDCl_3$) δ 15.96. Analytical calculated for $C_{15}H_{21}N_2O_4P$: C, 55.53; H, 6.53; N, 8.64. Found: C, 55.47; H, 6.51; N, 8.61

Dimethyl[1-butyl-2-(3,5-dimethiylphenyl)-2,3-dihydro-3-oxo-pyrazol-4-yl]phosphonate (compound 5d). The reaction is carried out using 5.8 mmol of structure 2 to afford the crude product as a pale yellow oil (1.6 g, 4.4 mmol, 80%). The crude product is purified by radial chromatography (IPA:EtOAc; 2:8) to afford the product as an off-white solid (700 mg, 2.0 mmol, 36%): $^1H$ NMR (400 MHz, $CDCl_3$) δ 7.93 (d, J=4.6 Hz, 1H), 7.03 (s, 1H), 6.93 (s, 2H), 3.84 (d, J=11.6 Hz, 6H), 3.68 (t, J=7.0 Hz, 2H), 2.36 (s, 6H), 1.49 (quintet, J=7.3 Hz, 2H), 1.20 (hextet, J=7.2 Hz, 2H), 0.85 (t, J=7.4 Hz, 3H); $^{13}C$ NMR (100 MHz, $CDCl_3$) δ 163.9 (d, J=13.7 Hz), 147.1 (d, J=19.1 Hz), 139.3, 132.9, 130.3, 123.8, 93.2 (d, J=223.2 Hz), 53.0 (d, J=6.1 Hz), 50.1, 30.1, 21.2, 19.5, 13.3; $^{31}P$ NMR (162 MHz, $CDCl_3$) δ 16.07. Analytical calculated for $C_{17}H_{25}N_2O_4P$: C, 57.93; H, 7.15; N, 7.95. Found: C, 57.77; H, 7.07; N, 7.90.

Example 2

Activity as Chemical Hybridizing Agents

The chemical hybridizing agent assay conditions for male sterility of cereals is demonstrated in wheat by the following method. The compounds of structure 3 and analogs are applied at a rate of 50–1000 μg/plant to cause pollen sterility. The male gametocidal activity is determined on the wheat variety 'OSLO', a double-dwarf hard red spring wheat. The wheat seed is planted to a depth of 0.5 to 1 inch (1–2.5 cm) in a 6-inch long (15 cm) conetainer (a cone shaped container, one seed per conetainer). The conetainers are filled with Metromix 200 potting soil supplemented with a slow release fertilizer, Osmocote and Sierra combined at 93 g/cu ft soil for a NPK of 31-20-24. Micromax with micronutrients is added at 17 g/cu ft rate. Fertilizer supplier is Hummerts, Earth City, Mo. 63045. The RLC-4 conetainers are 1×6 inch (2.5×15 cm) with a capacity of 4 cu in. (Stuewe & Sons, Inc., Corvallis, Oreg., 97333-9461). These are loaded into racks of 100 that occupy a 1.0 ft by 1.0 ft area. After seeding, the racks are placed in growth chambers with 14/10 hour day/night cycle at 18° C. These chambers are equipped with metal halide lamps that deliver approximately 300 $\mu E/m^2$/sec. Humidity is maintained at 50%, and plants are watered as needed. Approximately six weeks after seeding, wheat plants are selected for chemical application at or just prior to flag-leaf emergence from the boot (Feekes Scale 7.5–8.0) (Large, 1954. *Plant Pathology* 3:128–129). Plants are placed in a rack containing cardboard dividers to prevent each from being cross contaminated by an adjacent spray. The following procedures are used to evaluate the activity of the compounds of the invention for inducing male sterility in cereals. The plant heights vary and as uniformity is required for chemical application, the top 0–10 cm are removed by excision, such that the plant height is flush with the top of the divider. Prior to application, a 50 mL solution of DMSO (dimethylsulfoxide) containing the chemical hybridizing agent is diluted with 150 mL of water containing 1% SILWETL-77 surfactant (Witco Corp., Greenwich, Conn. 06831-2559) plus 2% humectant (glycerin, supplied by VWR Scientific Products Co.). The formulated chemicals are applied foliarly as an atomized spray onto the plants. After application, the plants are moved into growth chambers and allowed to grow until the heads emerge from the boot. Prior to anther extrusion (approximately 10 to 14 days after treatment), the plants are placed back into dividers in order to isolate the seed heads and to prevent cross-pollination. The plants are moved to a greenhouse, which has similar environmental conditions as the growth chambers. Approximately one week later (3 weeks after treatment (WAT) and at anther extrusion), open head morphology ratings are initiated. Plants are rated four times over a period of eight days (Table 2). The chemical hybridizing agent Genesis® (a registered Trade Mark of the Monsanto Co) is used as the positive control and for comparative purposes as to the rate of application and the efficacy as determined by percent sterility. The negative control is treatment of the wheat plants with the compounds making up the formulation of surfactant and humectant without the chemical compositions being assayed as chemical hybridizing agents. The data in Table 2 is expressed as % Sterility=(1−(Ave. normalized seed counts of sample/Ave. normalized seed counts of controls))*100 with the treatments comprising foliar application and rate titration at Feekes stage 8, across five replicates. Approximately two weeks after open head ratings are completed (six WAT), seed counts are collected.

Tables 2–4 summarizes typical results obtained in the evaluation of compounds of the structure 3, 4, 5, 8, and 10.

TABLE 2

Growth chamber/greenhouse evaluation of selected compounds of structures 3, 4 and 10

| Compound | $R^1$ | $R^2$ | $R^3$ | $R^4$ | $R^5$ | Rate µg/plant | Feekes | Sterility (%) |
|---|---|---|---|---|---|---|---|---|
| 3a | 4-ClPh | H | H | $CH_3$ | $CH_3$ | 500 | 8 | 92 |
|  |  |  |  |  |  | 250 | 8 | 79 |
|  |  |  |  |  |  | 125 | 8 | 34 |
|  |  |  |  |  |  | 50 | 8 | 39 |
|  |  |  |  |  |  | 500 | 6 | 49 |
|  |  |  |  |  |  | 250 | 6 | 0 |
|  |  |  |  |  |  | 125 | 6 | 0 |
|  |  |  |  |  |  | 50 | 6 | 27 |
| 3b | 4-FPh | H | H | $CH_3$ | $CH_3$ | 1000 | 8 | 98 |
|  |  |  |  |  |  | 500 | 8 | 91 |
|  |  |  |  |  |  | 250 | 8 | 90 |
|  |  |  |  |  |  | 125 | 8 | 30 |
|  |  |  |  |  |  | 50 | 8 | 23 |
| 3c | 2-ClPh | H | H | $CH_3$ | $CH_3$ | 1000 | 8 | 36 |
|  |  |  |  |  |  | 500 | 8 | 53 |
|  |  |  |  |  |  | 250 | 8 | 18 |
|  |  |  |  |  |  | 125 | 8 | 29 |
|  |  |  |  |  |  | 50 | 8 | 25 |
| 3d | 4-BrPh | H | H | $CH_3$ | $CH_3$ | 1000 | 8 | 54 |
|  |  |  |  |  |  | 500 | 8 | 15 |
|  |  |  |  |  |  | 250 | 8 | 17 |
|  |  |  |  |  |  | 125 | 8 | 0 |
|  |  |  |  |  |  | 50 | 8 | 0 |
| 3e | cyclo-hexyl | H | H | $CH_3$ | $CH_3$ | 1000 | 8 | 44 |
|  |  |  |  |  |  | 500 | 8 | 26 |
|  |  |  |  |  |  | 250 | 8 | 17 |
|  |  |  |  |  |  | 125 | 8 | 3 |
|  |  |  |  |  |  | 50 | 8 | 15 |
| 10a | 4-ClPh | H | Ph | $CH_3$ | $CH_3$ | 1000 | 8 | 45 |
|  |  |  |  |  |  | 500 | 8 | 18 |
|  |  |  |  |  |  | 250 | 8 | 27 |
|  |  |  |  |  |  | 125 | 8 | 0 |
|  |  |  |  |  |  | 50 | 8 | 1 |
| 10b | 3,5-diMePh | H | Ph | $CH_3$ | $CH_3$ | 1000 | 8 | 45 |
|  |  |  |  |  |  | 500 | 8 | 33 |
|  |  |  |  |  |  | 250 | 8 | 11 |
|  |  |  |  |  |  | 125 | 8 | 0 |
|  |  |  |  |  |  | 50 | 8 | 5 |
| 4a | 4-ClPh | $CH_2$(4-ClPh) | H | $CH_3$ | $CH_3$ | 500 | 8 | 93 |
|  |  |  |  |  |  | 250 | 8 | 93 |
|  |  |  |  |  |  | 125 | 8 | 80 |
|  |  |  |  |  |  | 50 | 8 | 48 |
|  |  |  |  |  |  | 500 | 6 | 34 |
|  |  |  |  |  |  | 250 | 6 | 9 |
|  |  |  |  |  |  | 125 | 6 | 0 |
|  |  |  |  |  |  | 50 | 6 | 0 |
| 4b | 4-ClPh | $CH_2$(2-$NO_2$Ph) | H | $CH_3$ | $CH_3$ | 500 | 8 | 94 |
|  |  |  |  |  |  | 250 | 8 | 57 |
|  |  |  |  |  |  | 125 | 8 | 0 |
|  |  |  |  |  |  | 50 | 8 | 16 |
|  |  |  |  |  |  | 500 | 6 | 0 |
|  |  |  |  |  |  | 250 | 6 | 0 |
|  |  |  |  |  |  | 125 | 6 | 0 |
|  |  |  |  |  |  | 50 | 6 | 0 |
| 3g | 3,5-diMePh | H | H | $CH_3$ | H | 500 | 8 | 15 |
|  |  |  |  |  |  | 250 | 8 | 0 |
|  |  |  |  |  |  | 125 | 8 | 17 |
|  |  |  |  |  |  | 50 | 8 | 38 |
|  |  |  |  |  |  | 500 | 6 | 6 |

TABLE 2-continued

Growth chamber/greenhouse evaluation of selected compounds of structures 3, 4 and 10

| Compound | R$^1$ | R$^2$ | R$^3$ | R$^4$ | R$^5$ | Rate μg/plant | Feekes | Sterility (%) |
|---|---|---|---|---|---|---|---|---|
|  |  |  |  |  |  | 250 | 6 | 12 |
|  |  |  |  |  |  | 125 | 6 | 3 |
|  |  |  |  |  |  | 50 | 6 | 0 |
| 3h | 4-ClPh | H | H | CH$_3$ | H | 500 | 8 | 15 |
|  |  |  |  |  |  | 250 | 8 | 9 |
|  |  |  |  |  |  | 125 | 8 | 12 |
|  |  |  |  |  |  | 50 | 8 | 31 |
|  |  |  |  |  |  | 500 | 6 | 47 |
|  |  |  |  |  |  | 250 | 6 | 22 |
|  |  |  |  |  |  | 125 | 6 | 3 |
|  |  |  |  |  |  | 50 | 6 | 0 |
| 4c | 4-ClPh | CH$_2$(2-NO$_2$Ph) | H | H | H | 500 | 8 | 67 |
|  |  |  |  |  |  | 250 | 8 | 0 |
|  |  |  |  |  |  | 125 | 8 | 4 |
|  |  |  |  |  |  | 50 | 8 | 0 |
|  |  |  |  |  |  | 500 | 6 | 21 |
|  |  |  |  |  |  | 250 | 6 | 0 |
|  |  |  |  |  |  | 125 | 6 | 0 |
|  |  |  |  |  |  | 50 | 6 | 0 |
| 3j | 4-ClPh | H | H | H | H | 500 | 8 | 12 |
|  |  |  |  |  |  | 250 | 8 | 0 |
|  |  |  |  |  |  | 125 | 8 | 13 |
|  |  |  |  |  |  | 50 | 8 | 31 |
|  |  |  |  |  |  | 500 | 6 | 35 |
|  |  |  |  |  |  | 250 | 6 | 0 |
|  |  |  |  |  |  | 125 | 6 | 7 |
|  |  |  |  |  |  | 50 | 6 | 4 |
| 3k | 3,5-diCH$_3$Ph | H | H | H | H | 500 | 8 | 9 |
|  |  |  |  |  |  | 250 | 8 | 9 |
|  |  |  |  |  |  | 125 | 8 | 33 |
|  |  |  |  |  |  | 50 | 8 | 32 |
|  |  |  |  |  |  | 500 | 6 | 0 |
|  |  |  |  |  |  | 250 | 6 | 4 |
|  |  |  |  |  |  | 125 | 6 | 17 |
|  |  |  |  |  |  | 50 | 6 | 32 |
| 3l | 3,5-diCH$_3$Ph | H | H | CH$_3$ | K$^+$ | 500 | 8 | 39 |
|  |  |  |  |  |  | 250 | 8 | 24 |
|  |  |  |  |  |  | 125 | 8 | 28 |
|  |  |  |  |  |  | 50 | 8 | 12 |
|  |  |  |  |  |  | 500 | 6 | 54 |
|  |  |  |  |  |  | 250 | 6 | 39 |
|  |  |  |  |  |  | 125 | 6 | 17 |
|  |  |  |  |  |  | 50 | 6 | 0 |
| 3m | 4-ClPh | H | H | CH$_3$ | K$^+$ | 500 | 8 | 15 |
|  |  |  |  |  |  | 250 | 8 | 16 |
|  |  |  |  |  |  | 125 | 8 | 20 |
|  |  |  |  |  |  | 50 | 8 | 28 |
|  |  |  |  |  |  | 500 | 6 | 43 |
|  |  |  |  |  |  | 250 | 6 | 31 |
|  |  |  |  |  |  | 125 | 6 | 0 |
|  |  |  |  |  |  | 50 | 6 | 23 |
| 3n | 3,5-diCH$_3$Ph | H | H | H | K$^+$ | 500 | 8 | 20 |
|  |  |  |  |  |  | 250 | 8 | 4 |
|  |  |  |  |  |  | 125 | 8 | 11 |
|  |  |  |  |  |  | 50 | 8 | 15 |
|  |  |  |  |  |  | 500 | 6 | 31 |
|  |  |  |  |  |  | 250 | 6 | 10 |
|  |  |  |  |  |  | 125 | 6 | 7 |
|  |  |  |  |  |  | 50 | 6 | 7 |
| Genesis ® |  |  |  |  |  | 500 | 8 | 90 |
|  |  |  |  |  |  | 250 | 8 | 78 |
|  |  |  |  |  |  | 125 | 8 | 93 |
|  |  |  |  |  |  | 50 | 8 | 67 |
|  |  |  |  |  |  | 500 | 6 | 97 |
|  |  |  |  |  |  | 250 | 6 | 89 |
|  |  |  |  |  |  | 125 | 6 | 86 |
|  |  |  |  |  |  | 50 | 6 | 36 |
| no compound |  |  |  |  |  | — | 8 | 0 |
|  |  |  |  |  |  | — | 6 | 0 |

TABLE 3

Biological activity of selected compound 8a.

| Compound | R¹ | R² | R³ | R⁴ | R⁵ | Rate μg/plant | Sterility (%) |
|---|---|---|---|---|---|---|---|
| 8a | 4-BrPh | CH₃CH₂ | H | CH₃ | CH₃ | 1000 | 15 |
|   |   |   |   |   |   | 500 | 25 |
|   |   |   |   |   |   | 250 | 44 |
|   |   |   |   |   |   | 125 | 0 |
|   |   |   |   |   |   | 50 | 12 |
| Genesis ® |   |   |   |   |   | 1000 | 99 |
|   |   |   |   |   |   | 500 | 91 |
|   |   |   |   |   |   | 250 | 93 |
|   |   |   |   |   |   | 125 | 64 |
|   |   |   |   |   |   | 50 | 48 |
| No compound |   |   |   |   |   | — | 0 |

TABLE 4

Biological activity of selected compounds of structure 5

| Compound | R¹ | R⁴=R⁵ | R³ | R⁶ | Rate μg/plant | Sterility (%) |
|---|---|---|---|---|---|---|
| 5a | 4-ClPh | CH₃ | H | Et | 1000 | 10 |
|   |   |   |   |   | 500 | 29 |
|   |   |   |   |   | 250 | 66 |
|   |   |   |   |   | 125 | 26 |
|   |   |   |   |   | 50 | 11 |
| 5b | 4-ClPh | CH₃ | H | Cyclohexyl | 1000 | 62 |
|   |   |   |   |   | 500 | 23 |
|   |   |   |   |   | 250 | 20 |
|   |   |   |   |   | 125 | 14 |
|   |   |   |   |   | 50 | 0 |
| 5c | 3,5-diCH₃Ph | CH₃ | H | Et | 1000 | 31 |
|   |   |   |   |   | 500 | 48 |
|   |   |   |   |   | 250 | 16 |
|   |   |   |   |   | 125 | 1 |
|   |   |   |   |   | 50 | 8 |
| 5d | 3,5-diCH₃Ph | CH₃ | H | Butyl | 1000 | 41 |
|   |   |   |   |   | 500 | 24 |
|   |   |   |   |   | 250 | 28 |
|   |   |   |   |   | 125 | 0 |
|   |   |   |   |   | 50 | 29 |
| Genesis ® |   |   |   |   | 1000 | 99 |
|   |   |   |   |   | 500 | 91 |
|   |   |   |   |   | 250 | 93 |
|   |   |   |   |   | 125 | 64 |
|   |   |   |   |   | 50 | 48 |
| no compound |   |   |   |   | — | 0 |

The results of screening for percent sterility activity of 375 compounds of the phosphonopyrazolinones and phosphonopyrazolines synthesized using the method described in Example 2 are shown in Table 5. Of the 375 compounds screened, 22 (5.9%) have male gametocidal activity, of which 4 (1.1% of those initially screened) have greater than 90% activity, a level that is generally considered sufficient for commercial development. The gametocidal activity and the rates at which the 22 compounds are shown to be effective are summarized in Tables 2, 3 and 4.

TABLE 5

Frequency of gametocidal activity of the compounds in the phosphonopyrazolinones and phosphonopyrazolines class

| | All compounds (% of screened) |
|---|---|
| screened | 375 |
| actives | 22 (5.9) |

TABLE 5-continued

Frequency of gametocidal activity of the compounds in the phosphonopyrazolinones and phosphonopyrazolines class

| | All compounds (% of screened) |
|---|---|
| 25–50% sterility | 13 (3.5) |
| 50–90% sterility | 5 (1.3) |
| >90% sterility | 4 (1.1) |

Although the compositions and methods of this invention have been described in terms of preferred embodiments, it will be apparent to those of skill in the art that variations may be made to the synthetic methods, compositions, formulations and uses described herein without departing from the concept, spirit and scope of the invention. All such similar substitutes and modifications apparent to those skilled in the art are deemed to be within the scope of the invention as defined by the appended claims.

All patents, patent applications, and scientific articles referenced herein are hereby incorporated by reference in their entirety for all purposes.

What is claimed is:

1. A method of inducing male sterility in a plant comprising treating the plant or a seed thereof with a composition comprising a gametocidally effective amount of one or more compounds of formula I or II

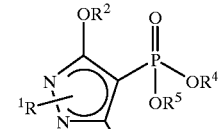

I

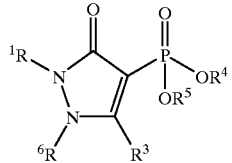

II and an agronomically acceptable carrier, wherein:

R¹ is selected from the group consisting of hydrogen, alkyl, aryl, heteroaryl, benzyl and C3–C8 cycloalkyl;

R² is selected from the group consisting of hydrogen, alkyl, benzyl, C1–C8 alkenyl, and a salt;

R³ is selected from the group consisting of hydrogen, alkyl, aryl and heteroaryl;

R⁴ is selected from the group consisting of hydrogen, alkyl, phenyl, and a salt;

R⁵ is selected from the group consisting of hydrogen, alkyl, phenyl, and a salt;

R⁶ is selected from the group consisting of alkyl, aryl and heteroaryl;

alkyl is selected from the group consisting of C1–C8;

aryl is selected from the group consisting of phenyl; naphthyl; phenyl substituted with 1–5 groups selected from halogen, trihalomethyl, C1–C8 alkyl, C1–C8 alkoxy, nitro and cyano; and naphthyl substituted with 1–5 groups selected from halogen, trihalomethyl, C1–C8 alkyl, C1–C8 alkoxy, nitro and cyano;

benzyl is selected from the group consisting of benzyl and benzyl substituted with 1–3 groups selected from halogen, trihalomethyl, C1–C8 alkyl, C1–C8 alkoxy, nitro and cyano; and heteroaryl is selected from the group consisting of pyridyl and pyridyl substituted with 1–4 groups selected from halogen, trihalomethyl, C1–C8 alkyl, C1–C8 alkoxy, nitro and cyano.

2. The method of claim 1, wherein the plant is a monocot.

3. The method of claim 2, wherein the plant is a graminaceous monocot.

4. The method of claim 3, wherein the plant is a wheat plant.

* * * * *